United States Patent
Pevarello et al.

(10) Patent No.: US 6,303,819 B1
(45) Date of Patent: Oct. 16, 2001

(54) SUBSTITUTED 2-BENZYLAMINO-2-PHENYL-ACETAMIDE COMPOUNDS

(75) Inventors: Paolo Pevarello, Pavia; Mario Varasi, Milan; Patricia Salvati, Arese, all of (IT); Claes Post, Sigtuna (SE)

(73) Assignee: Newron Pharmaceuticals S.p.A., Gerenzano (IT)

( * ) Notice: Subject to any disclaimer, the term of this patent is extended or adjusted under 35 U.S.C. 154(b) by 0 days.

(21) Appl. No.: 09/581,254

(22) PCT Filed: Dec. 12, 1998

(86) PCT No.: PCT/EP98/08158

§ 371 Date: Sep. 11, 2000

§ 102(e) Date: Sep. 11, 2000

(87) PCT Pub. No.: WO99/35123

PCT Pub. Date: Jul. 15, 1999

(30) Foreign Application Priority Data

Dec. 31, 1997 (GB) .................................................. 9727521

(51) Int. Cl.$^7$ ........................ C07C 233/05; A61K 31/165
(52) U.S. Cl. ......................... 564/165; 564/162; 564/164; 514/618; 514/619; 514/620
(58) Field of Search ................... 514/618, 619, 514/620; 564/162, 164, 165

(56) References Cited

U.S. PATENT DOCUMENTS 5,670,546 * 9/1997 Park et al. ........................... 514/620
5,688,830   11/1997 Berger et al. .
5,723,489 * 3/1998 Sher et al. ........................... 514/620

* cited by examiner

Primary Examiner—Shailendra Kumar
(74) Attorney, Agent, or Firm—Arent Fox Kintner Plotkin & Kahn PLLC

(57) ABSTRACT

Compounds which are substituted 2-benzylamino-2-phenyl-acetamide compounds of formula (I)

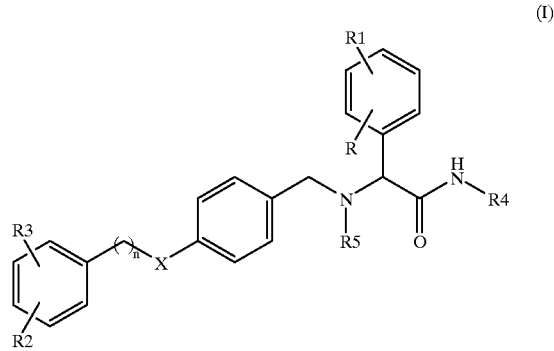

wherein:
n is zero, 1, 2 or 3;
X is —O—, —S—, —CH$_2$— or —NH—;
each of R, R$_1$, R$_2$ and R$_3$, independently, is hydrogen, C$_1$–C$_6$ alkyl, halogen, hydroxy, C$_1$–C$_6$ alkoxy or trifluoromethyl;
each of R$_4$ and R$_5$, independently, is hydrogen, C$_1$–C$_6$ alkyl or C$_3$–C$_7$ cycloalkyl; or pharmaceutically acceptable salts thereof, are useful in treating conditions such as chronic or neuropathic pain.

9 Claims, No Drawings

SUBSTITUTED 2-BENZYLAMINO-2-PHENYL-ACETAMIDE COMPOUNDS

This application is a 371 of PCT/EP98/08159 filed Dec. 12, 1998.

The present invention relates to novel substituted 2-benzylamino-2-phenyl-acetamide compounds, to a process for their preparation, to pharmaceutical composition containing them and to their use as therapeutic agents.

In particular, the compounds provided by the present invention are sodium channel blockers, and thus exhibit useful pharmacological properties, especially for the treatment and alleviation of chronic and neuropathic pain. Chronic and neuropathic pain are associated with prolonged tissue damage or injuries to the peripheral or central nervous system and result from a number of complex changes in nociceptive pathways, including ion channel function. Clinical manifestations of chronic pain include a sensation of burning or electric shock, feelings of bodily distortion, allodynia and hyperpathia.

Despite the large number of available analgesics, their use is limited by severe side effects and modest activity in some pain conditions. Therefore there is still a clear need to develop new compounds.

Accordingly, one object of the present invention is to provide novel compound having the following formula (I)

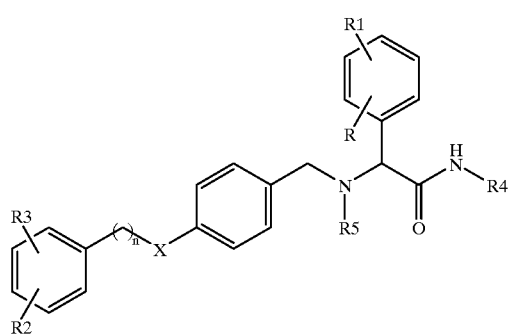

(I)

wherein:

n is zero, 1, 2 or 3;

X is —O—, —S—, —CH$_2$— or —NH—; each of R, R$_1$, R$_2$ and R$_3$, independently, is hydrogen, C$_1$–C$_6$ alkyl, halogen, hydroxy, C$_1$–C$_6$ alkoxy or trifluoromethyl;

each of R$_4$ and R$_5$, independently, is hydrogen, C$_1$–C$_6$ alkyl or C$_3$–C$_7$ cycloalkyl; and the pharmaceutically acceptable salts thereof.

A —(CH$_2$)$_n$— chain may be a branched or straight chain.

Alkyl and alkoxy groups may be branched or straight groups. Representative examples of C$_1$–C$_6$ alkyl groups include C$_1$–C$_4$ alkyl groups such as methyl, ethyl, n- and iso-propyl, n-, iso-, sec- and tert-butyl.

Representative examples of C$_1$–C$_6$ alkoxy groups include C$_1$–C$_4$ alkoxy groups such as methoxy and ethoxy.

A C$_3$–C$_7$ cycloalkyl group is for instance cyclopropyl, cyclopentyl or cyclohexyl, in particular cyclopentyl or cyclohexyl.

A halogen atom is fluorine, bromine, chlorine or iodine, in particular, chlorine or fluorine.

Pharmaceutically acceptable salts of the compounds of the invention include acid addition salts with inorganic, e.g. nitric, hydrochloric, hydrobromic, sulphuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids.

The compounds of the invention have asymmetric carbon atoms and therefore they can exist either as racemic mixtures or as individual optical isomers (enantiomers).

Accordingly, the present invention also include within its scope all the possible isomers and their mixtures and both the metabolites and the pharmaceutically acceptable bio-precursors (otherwise known as pro-drugs) of the compounds of the invention.

Preferred compounds of the invention are the compounds of formula (I) wherein n is 1 or 2;

X is —O—;

each of R, R$_1$, R$_2$ and R$_3$, independently, is hydrogen, or halogen;

R$_4$ and R$_5$ are hydrogen; and the pharmaceutically acceptable salts thereof.

Examples of specific compounds of the invention are:

2-[4-benzyloxybenzylamino]-2-phenyl-acetamide;
2-[4-(3-fluorobenzyloxy)benzylamino]-2-phenyl-acetamide;
2-[4-(3-chlorobenzyloxy)benzylamino]-2-phenyl-acetamide;
2-[4-(3-bromobenzyloxy)benzylamino]-2-phenyl-acetamide;
2-[4-(2-fluorobenzyloxy)benzylamino]-2-phenyl-acetamide;
2-[4-(3-fluorobenzyloxy)benzylamino]-2-(2-fluorophenyl)-acetamide;
2-[4-(3-fluorobenzyloxy)benzylamino]-2-(3-fluorophenyl)-acetamide; and
2-[4-(3-chlorobenzyloxy)benzylamino]-2-(3-fluorophenyl)-acetamide, if the case either as a single isomer or as a mixture thereof, and the pharmaceutically acceptable salts thereof.

Object of the present invention is also to provide a compound of formula (I), as defined above, or a pharmaceutically acceptable salt thereof for use as a therapeutic substance, in particular for treating chronic and neuropathic pain.

An aspect of this invention relates to the use of a compound of formula (I), as defined above, or a pharmaceutically acceptable salt thereof in the manufacture of a medicament for use in treating chronic and neuropathic pain.

A further aspect of this invention relates to a method of treating a mammal, including humans, in need of a sodium channel-blocking agent, said method comprising administering thereto an effective amount of a compound of formula (I) or a pharmaceutically acceptable salt thereof.

Neuropathic pain conditions in a mammal can thus be alleviated and treated. Examples of neuropathic pain conditions responsive to sodium channel-blocking agents include:

peripheral neuropathies, such as trigeminal neuralgia, postherapeutic neuralgia, diabetic neuropathy, glossopharyngeal neuralgia, radiculopathy, and neuropathy secondary to metastatic infiltration, adiposis dolorosa and burn pain; and central pain conditions following stroke, thalamic lesions and multiple sclerosis.

'Treatment' as used herein covers any treatment of a condition in a mammal, particularly a human, and includes:

(i) preventing the disease from occurring in a subject which may be predisposed to the disease, but has not yet been diagnosed as having it;

(ii) inhibiting the condition, i.e., arresting its development; or (iii) relieving the condition, i.e., causing regression of the disease.

The term 'disease state which is alleviated by treatment with a sodium channel blocker' as used herein is intended to cover all disease states which are generally acknowledged in the art to be usefully treated with sodium channel blockers in general, and those disease states which have been found to be usefully treated by the specific sodium channel blocker of our invention, the compound of formula (I).

The compounds of the invention and the salts thereof can be obtained, for instance, by a process comprising:

a) reacting a compound of formula (II)

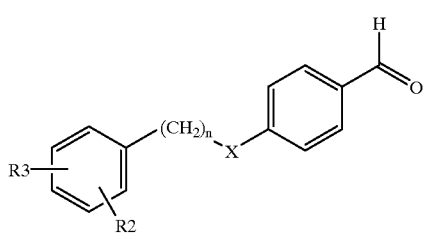
(II)

wherein n, $R_2$, $R_3$ and X are as defined above, with a compound of formula (III)

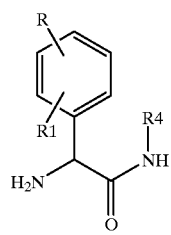
(III)

wherein R, $R_1$ and $R_4$ are as defined above, thus obtaining a compound of formula (I) in which $R_5$ is hydrogen; or b) reacting a compound of formula (IV)

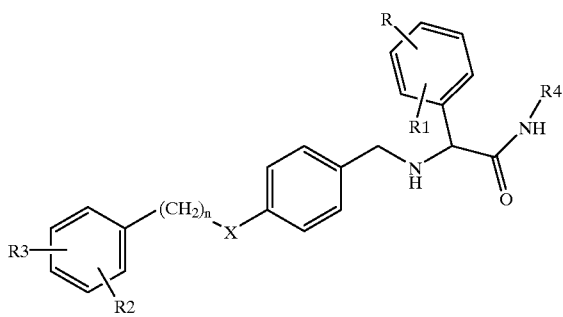
(IV)

wherein R, $R_1$, $R_2$, $R_3$, $R_4$, n and X are as defined above, with a compound of formula (V), (VI) or (VII)

R'$_5$W       (V)

R"$_5$CHO       (VI)

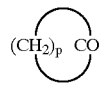
(VII)

wherein W is a halogen atom; R'$_5$ is a $C_1$–$C_6$ alkyl or $C_3$–$C_7$ cycloalkyl and R"$_5$ is hydrogen or $C_1$–$C_5$ alkyl, and p is 2–6, thus obtaining a compound of the invention in which $R_5$ is $C_1$–$C_6$ alkyl or $C_3$–$C_7$ cycloalkyl; and, if desired, converting a compound of the invention into another compound of the invention and/or, if desired, converting a compound of the invention into a pharmaceutically acceptable salt and/or, if desired, converting a salt into a free compound.

All the processes described hereabove are analogy processes and can be carried out according to well known methods in organic chemistry.

A compound of formula (IV) is a compound of formula (I) in which $R_5$ is hydrogen.

The reaction of a compound of formula (II) with a compound of formula (III) to give a compound of formula (I) or (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride.

Occasionally molecular sieves can be added to the reaction mixture for facilitating the reaction.

In a compound of formula (V) the halogen W is preferably iodine. The alkylation reaction of a compound of formula (IV) with a compound of formula (V) can be carried out in a suitable organic solvent, such as an alcohol, e.g. methanol, ethanol or isopropanol, in particular in ethanol, at a temperature ranging from about 0° C. to about 50° C.

The alkylation reaction of a compound of formula (IV) with an aldehyde of formula (VI) or (VII) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

A compound of the invention can be converted, as stated above, into another compound of the invention by known methods. Process-variant b) above may be regarded as an example of optional conversion of a compound of the invention into another compound of the invention.

Also the optional salification of a compound of the invention as well as the conversion of a salt into the free compound may be carried out by conventional methods.

The compounds of formula (II) and (III), (V), (VI) and (VII) are known compounds or can be obtained by known methods.

When in the compounds of the present invention and in the intermediate-products thereof, groups are present, which need to be protected before submitting them to the hereabove illustrated reactions, they may be protected before being reacted and then deprotected according to methods well known in organic chemistry.

Pharmacology

As stated above, the compounds of the invention are sodium channel-blocking agents, as proven for instance by the fact that they bind to site-2 (labeled by $^3$H-Batrachotoxin) on the rat brain sodium channel.

Interaction of the compounds with the site 2 of the sodium channel was evaluated in rat brain membranes using the $^3$H-batrachotoxin as ligand, according to published methods (Catterall, W. A., J. Biol. Chem., 1981, 256, 8922–8927).

For instance, for the representative compound of the (R)-2-[4-(3-fluorobenzyloxy)benzylamino]-2-phenyl-acetamide, methanesulfonate (internal code PNU 190296 E) the following test data were obtained.

TABLE 1

| Compound | Na+ channel block $^3$H-Batrachotoxin binding ($\mu$M) |
|---|---|
| PNU 190296E | 0.39 |

In view of their biological activity, the compounds of the invention are useful in therapy in the regulation of physiological phenomena related to sodium channel blockade, including arrhythmia, convulsion, pain associated with damage or permanent alteration of the peripheral or central nervous system, for example peripheral neuropathies, such as trigeminal neuralgia, postherapeutic neuralgia, diabetic neuropathy, raticulopathy, glossopharyngeal neuralgia, and neuropathy secondary to metastatic infiltration, adiposis dolorosa, and burn pain; and central pain conditions following stroke, thalamic lesions and multiple sclerosis.

The conditions of a patient in need of a sodium channel-blocking agent may thus be improved.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans e.g. for the representative compound of the invention (R)-2-[4-(3-fluorobenzyloxy)benzylamino]-2-phenyl-acetamide may range from about 1 to about 500 mg pro dose, from 1 to 5 times daily.

The invention includes pharmaceutical compositions comprising a compound of the invention, as an active principle, in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; desegregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspension.

The syrups may contain as carrier, for example, saccharose or saccharose with glycerine and/or mannitol and/or sorbitol.

The suspension and the emulsion may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

1. D-phenyglycinamide 30 g (0.149 mol) of D-phenylglycine methyl ester, hydrochloride were dissolved in dioxane (90 mL), then 90 mL of 30% NH$_4$OH solution were added dropwise. The mixture was stirred overnight, evaporated and the crude residue flash-chromatographed on silica gel using dichloromethane/methanol/30% NH$_4$OH; 165/35/3. The white solid obtained was dissolved in abs. EtOH and acidified with an excess of 10% HCl in ETOH. The solution was evaporated, taken up with diethyl ether (Et$_2$O), the white solid precipitated was filtered and washed with Et$_2$O, yielding 12.2 g (69%) of pure compound.

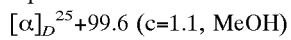

2. (R)-2-[4-(3-fluorobenzyloxy)benzylamino]-2-phenyl-acetamide, methanesulfonate A mixture of D-phenylglycinamide hydrochloride (4.45 g; 0.022 mol) and 3A molecular sieves (4.45 g) in MeOH (150 mL) was stirred under nitrogen for 10 minutes, then treated with sodium cyanoborohydride (1.09 g; 0.016 mol) and 4-(3-fluorobenzyloxy)benzaldehyde (5 g; 0.022 mol). The mixture was stirred at room temperature for 4 hours, then filtered, the residue evaporated and flash-chromatographed on silica gel using dichloromethane/methanol/30% NH4OH; 95/5/0.5) as eluant. 5.3 g (53%) of a crystalline white solid were obtained after treatment with an excess of methanesulfonic acid in ethyl acetate and filtration.

m.p. 227–231° C.;

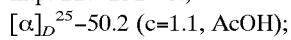

Elemental Analysis:

| Atom | Calc. | Found |
|---|---|---|
| C | 59.98 | 59.17 |
| H | 5.47 | 5.46 |
| N | 6.08 | 6.04 |
| S | 6.96 | 7.30 |

Analogously, starting from the appropriate aldehyde and aminoamide, the following compounds can be prepared:

2-[4-benzyloxybenzylamino]-2-phenyl-acetamide methanesulfonate;
2-[4-(3-chlorobenzyloxy)benzylamino]-2-phenyl-acetamide methanesulfonate;
2-[4-(3-bromobenzyloxy)benzylamino]-2-phenyl-acetamide methanesulfonate;
2-[4-(2-fluorobenzyloxy)benzylamino]-2-phenyl-acetamide methanesulfonate;
2-[4-(3-fluorobenzyloxy)benzylamino]-2-(2-fluorophenyl)-acetamide methanesulfonate;
2-[4-(3-fluorobenzyloxy)benzylamino]-2-(3-fluorophenyl)-acetamide methanesulfonate;
2-[4-(3-chlorobenzyloxy)benzylamino]-2-(3-fluorophenyl)-acetamide methanesulfonate;
2-[4-(3-fluorobenzylamino)benzylamino]-2-phenyl-acetamide methanesulfonate; and
2-[4-(3-fluorobenzylthio)benzylamino]-2-phenyl-acetamide methanesulfonate.

EXAMPLE 2

(R)-2-[[4-(3-fluorophenyloxy)benzyl]-2-methyl-amino]-2-phenyl-acetamide 4 g (0.011 mol) of (R)-2-[4-(3-fluorophenyloxy) benzylamino]-2-phenyl-acetamide were dissolved in methanol (50 mL) and 1.8 g (0.013 mol) of anhydrous potassium carbonate were added to the solution. Methyl iodide (1.5 mL; 0.025 mol) was dropped into the mixture which was stirred for 2 hours at room temperature and then evaporated to dryness. The crude residue was chromatographed on silica gel (eluant: chloroform/methanol; 95/5). 2.11 g (51%) of (R)-2-[[4-(3-fluorophenyloxy)benzyl]-2-methyl-amino]-2-phenyl-acetamide were obtained.

Elemental Analysis:

| Atom | Calc. | Found |
|------|-------|-------|
| C    | 73.00 | 73.35 |
| H    | 6.13  | 6.18  |
| F    | 5.02  | 5.00  |
| N    | 7.40  | 7.29  |

Analogously, the following compounds can be obtained and, if required, salified with a suitable acidic agent according to known methods:

(R)-2-[[4-(3-chlorophenyloxy)benzyl]-2-methyl-amino]-2-phenyl-acetamide;
(S)-2-[[4-(3-fluorophenyloxy)benzyl]-2-methyl-amino]-2-phenyl-acetamide;
(R)-2-[[4-(3-bromophenyloxy)benzyl]-2-methyl-amino]-2-phenyl-acetamide;
(R)-2-[[4-(3-fluorophenyloxy)benzyl]-2-ethyl-amino]-2-phenyl-acetamide;
(R)-2-[(4-phenyloxybenzyl)-2-methyl-amino]-2-phenyl-acetamide;
(S)-2-[(4-phenyloxybenzyl)-2-methyl-amino]-2-phenyl-acetamide; and
(R)-2-[[4-(3-fluorophenyloxy)benzyl]-2-cyclopropyl-amino]-2-phenyl-acetamide.

EXAMPLE 3

With the usual methods of pharmaceutical technique, preparation can be made of capsules having the following composition:

| 2-[4-(3-fluorobenzyloxy)benzylamino]-2-phenyl-acetamide, methanesulfonate | 50 mg |
|---|---|
| Talc | 2 mg |
| Corn starch | 2 mg |
| Microcristalline cellulose | 6 mg |
| Magnesium stearate | 1 mg |

What is claimed is:

1. A compound which is a substituted 2-benzylamino-2-phenyl acetamide of formula (I)

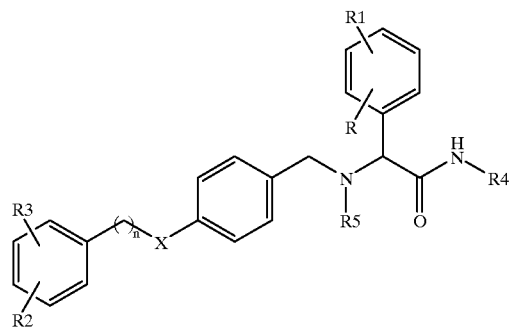

wherein:

n is zero, 1, 2 or 3;

X is —O—, —S—, —CH$_2$— or —NH—;

each of R, R$_1$, R$_2$ and R$_3$, independently, is hydrogen, C$_1$–C$_6$ alkyl, halogen, hydroxy, C$_1$–C$_6$ alkoxy or trifluoromethyl;

each of R$_4$ and R$_5$, independently, is hydrogen, C$_1$–C$_6$ alkyl or C$_3$–C$_7$ cycloalkyl; or a pharmaceutically acceptable salt thereof.

2. A compound according to claim 1, wherein n is 1 or 2;

X is —O—;

each of R, R$_1$, R$_2$ and R$_3$, independently, is hydrogen, or halogen;

R$_4$ and R$_5$ are hydrogen.

3. A compound according to claim 1, which is selected from:

2-[4-benzyloxybenzylamino]-2-phenyl-acetamide;
2-[4-(3-fluorobenzyloxy)benzylamino]-2-phenyl-acetamide;
2-[4-(3-chlorobenzyloxy)benzylamino]-2-phenyl-acetamide;
2-[4-(3-bromobenzyloxy)benzylamino]-2-phenyl-acetamide;
2-[4-(2-fluorobenzyloxy)benzylamino]-2-phenyl-acetamide;
2-[4-(3-fluorobenzyloxy)benzylamino]-2-(2-fluorophenyl)-acetamide;
2-[4-(3-fluorobenzyloxy)benzylamino]-2-(3-fluorophenyl)-acetamide; and
2-[4-(3-chlorobenzyloxy)benzylamino]-2-(3-fluorophenyl)-acetamide, if the case either as a single isomer or as a mixture thereof, or a pharmaceutically acceptable salt thereof.

4. A pharmaceutical composition comprising a pharmaceutically acceptable excipient and, as an active agent, a compound as defined in claim 1.

5. A compound as defined in claim 1, for use in a method of treatment of the human or animal body by therapy.

6. A compound as claimed in claim 5 for use in regulating a physiological condition related to sodium channel blockade.

7. A compound as claimed in claim 5, for use in treating chronic or neuropathic pain.

8. A method of treating a mammal, including a human, in need of a sodium channel-blocking agent, said method comprising administering thereto an effective amount of a compound of formula (I) or a pharmaceutically acceptable salt thereof.

9. A method according to claim 8 wherein the mammal is suffering from chronic or neuropathic pain.

\* \* \* \* \*